(12) United States Patent
Pelletier et al.

(10) Patent No.: US 9,798,039 B2
(45) Date of Patent: Oct. 24, 2017

(54) FREQUENCY BASED MEASUREMENT OF CHARACTERISTICS OF A SUBSTANCE

(71) Applicant: Halliburton Energy Services, Inc., Houston, TX (US)

(72) Inventors: Michael T. Pelletier, Houston, TX (US); William J. Soltmann, The Woodlands, TX (US); David L. Perkins, The Woodlands, TX (US); Raj Pai, Houston, TX (US); James E. Masino, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/899,436

(22) PCT Filed: Jul. 9, 2014

(86) PCT No.: PCT/US2014/045845
§ 371 (c)(1),
(2) Date: Dec. 17, 2015

(87) PCT Pub. No.: WO2016/007146
PCT Pub. Date: Jan. 14, 2016

(65) Prior Publication Data
US 2016/0202385 A1   Jul. 14, 2016

(51) Int. Cl.
*G01V 5/04* (2006.01)
*G01V 8/12* (2006.01)
(Continued)

(52) U.S. Cl.
CPC .............. *G01V 8/12* (2013.01); *E21B 47/102* (2013.01); *E21B 47/123* (2013.01); *E21B 49/00* (2013.01);
(Continued)

(58) Field of Classification Search
CPC ..... E21B 47/065; E21B 47/102; G01K 7/203; G01N 21/8422; G01N 21/31; G01N 2021/8438; G01N 2021/4126
See application file for complete search history.

(56) References Cited

U.S. PATENT DOCUMENTS

| | | |
|---|---|---|
| 4,982,080 A | 1/1991 | Wilson et al. |
| 8,770,835 B2 * | 7/2014 | Sroka .................... E21B 49/081 340/853.1 |

(Continued)

FOREIGN PATENT DOCUMENTS

WO    2014105071    7/2014

OTHER PUBLICATIONS

International Search Report and Written Opinion of PCT Application No. PCT/US2014/045845 dated Apr. 3, 2015: pp. 1-11.

(Continued)

*Primary Examiner* — Kenneth J Malkowski
(74) *Attorney, Agent, or Firm* — Chamberlain Hrdlicka

(57) ABSTRACT

In a downhole environment, utilizing one or more ICE modules, in response to detecting light by one or more channels of a light to voltage converter, the detected light is converted into one or more voltages. The light has previously interacted with a downhole substance and has been processed by an integrated computational element. The one or more voltages are converted into one or more analog frequencies. The one or more analog frequencies are converted into one or more digital frequencies. One or more intensities are determined from one or more digital frequencies. One or more components of the substance are determined in response to the determined one or more intensities.

20 Claims, 9 Drawing Sheets

(51) Int. Cl.
*E21B 47/10* (2012.01)
*E21B 49/00* (2006.01)
*G01N 21/84* (2006.01)
*E21B 47/12* (2012.01)
*G01V 3/18* (2006.01)
*E21B 49/08* (2006.01)

(52) U.S. Cl.
CPC .... *G01N 21/8422* (2013.01); *E21B 2049/085* (2013.01); *G01V 3/18* (2013.01)

(56) References Cited

U.S. PATENT DOCUMENTS

| | | | |
|---|---|---|---|
| 2003/0192692 A1* | 10/2003 | Tubel | E21B 41/00 166/250.15 |
| 2006/0142955 A1 | 6/2006 | Jones et al. | |
| 2009/0278552 A1 | 11/2009 | Jakkula et al. | |
| 2013/0032338 A1* | 2/2013 | Kalia | E21B 43/14 166/250.01 |
| 2013/0061899 A1* | 3/2013 | Tosi | G21H 1/103 136/202 |
| 2013/0284901 A1 | 10/2013 | Freese et al. | |
| 2014/0366640 A1* | 12/2014 | Sidhwa | G01F 1/56 73/861.12 |

OTHER PUBLICATIONS

Anonymous, ADNB-3532: "Low Power LED Integrated Slim Mouse Sensor," Avago Technologies Limited Data Sheet, May 2007: pp. 1-27.

* cited by examiner

100

200

300

400

500

700

800

900

FREQUENCY BASED MEASUREMENT OF CHARACTERISTICS OF A SUBSTANCE

TECHNICAL FIELD

The present disclosure relates generally to the measurement of characteristics of a substance using integrated computational elements, and more particularly, to systems and methods to measure characteristics of a substance, such as from a downhole source. Integrated computational elements may enable the measurement of various chemical or physical characteristics of the substance.

BACKGROUND

In producing substances from an oil and gas well, it is often advantageous to learn as much about the substances in the well as possible. Although some information can be obtained by downhole instruments and tools, additional information and improvements are desired. Integrated computational elements assist in identifying substances or substance characteristics.

BRIEF DESCRIPTION OF THE DRAWINGS

Illustrative embodiments of the present disclosure are described in detail below with reference to the attached drawing figures, which are incorporated by reference herein and wherein.

Figure 1:
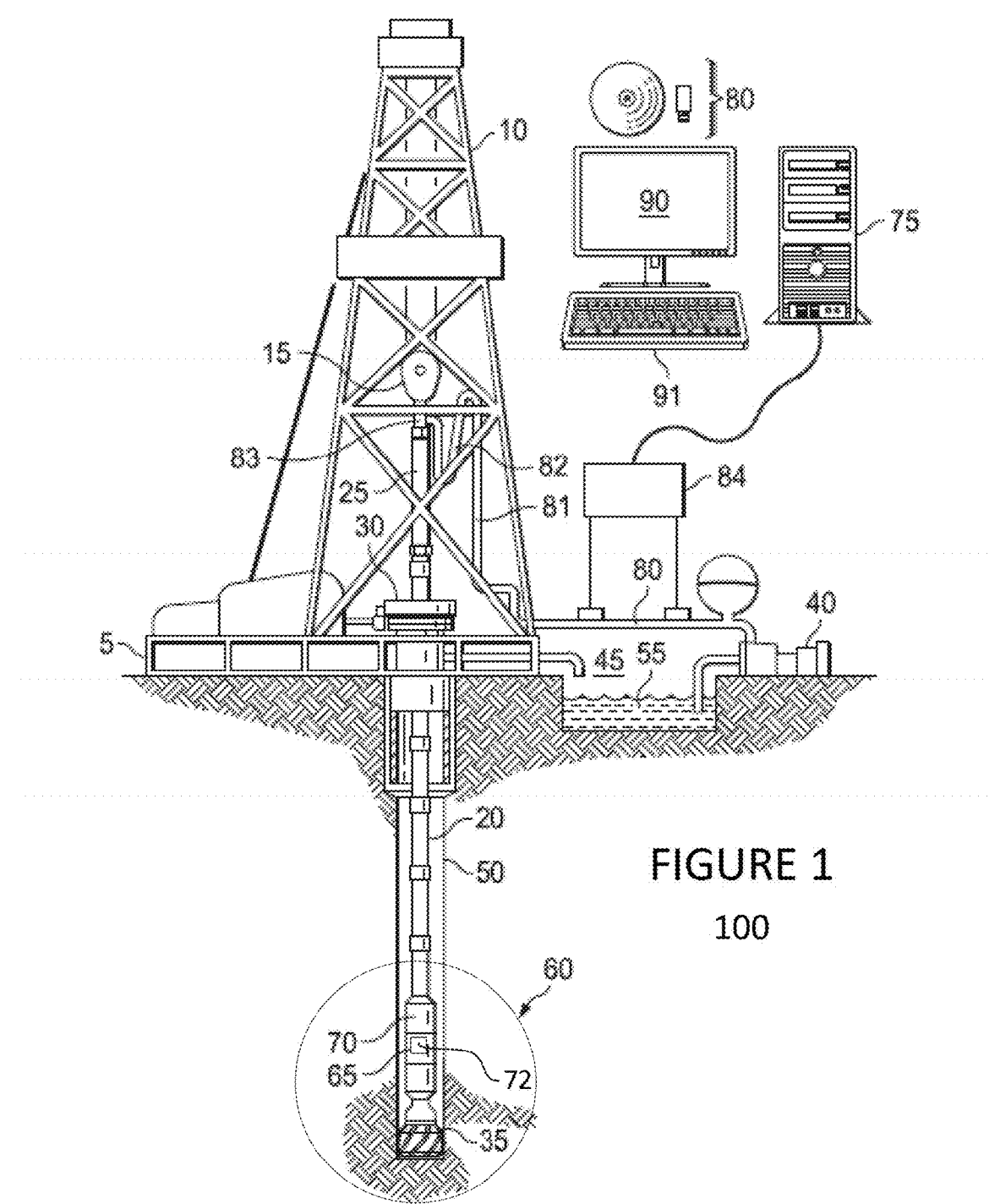
FIG. 1 is a schematic diagram of a logging-while-drilling environment according to an illustrative embodiment.

The illustrated figures are only exemplary and are not intended to assert or imply any limitation with regard to the environment, architecture, design, or process in which different embodiments may be implemented.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

In the drawings and description that follow, like parts are typically marked throughout the specification and drawings with the same reference numerals or coordinated numerals. The drawing figures are not necessarily to scale. Certain features of the invention may be shown exaggerated in scale or in somewhat schematic form and some details of conventional elements may not be shown in the interest of clarity and conciseness.

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to". Unless otherwise indicated, as used throughout this document, "or" does not require mutual exclusivity.

The various characteristics mentioned herein, as well as other features and characteristics described in more detail below will be readily apparent to those skilled in the art with the aid of this disclosure upon reading the following detailed description of the embodiments, and by referring to the accompanying drawings. Other means may be used as well.

The embodiments discussed herein may be utilized in various contexts to determine the properties of a substance in downhole environments utilizing at least one integrated computational element. A substance may include a single-phase flowable substance (e.g., a granulated solid) or a multi-phase flowable substance containing any combination of a solid, a liquid, or a gas (e.g., a gel, an emulsion, a mist, a smoke, etc.). For example, the embodiments may be utilized to determine properties of substances encountered in logging-while-drilling (LWD) environments, wireline, or other logging environments. Other applications, including non-drilling applications are contemplated.

Information about a substance can be derived through the interaction of electromagnetic radiation, e.g., light, with that substance. When the term "light" and derivatives thereof are used herein, it is also understood to mean electromagnetic radiation generally. The examples herein relate to light as an illustrative embodiment. The interaction changes the characteristics of the electromagnetic radiation to form a sample electromagnetic radiation. For example, interacted light changes with respect to frequency (and corresponding wavelength), intensity, polarization, or direction (e.g., through scattering, reflection, or refraction) when interacting with a substance. This sample electromagnetic radiation is processed to determine chemical or physical properties of the substance (e.g., compositional, thermal, physical, mechanical, and optical among others). More particularly, the sample electromagnetic radiation is processed to determine the presence and concentration of a particular material in the substance. For example, the processing may be utilized to determine a constituent of the downhole substance, such as methane, ethane, propane, aromatics, saturates, or water, based on changes in the characteristics of the electromagnetic radiation. As such, in certain applications, one or more properties of substances such as crude petroleum, gas, water, or other production fluids from a wellbore can be derived in situ, upon emergence out of an subterranean reservoir, as a result of the interaction between these substances and electromagnetic radiation.

As used herein, the term "characteristic" or "characteristic of interest" refers to a chemical, mechanical, or physical property of a substance or a sample of the substance. The characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be analyzed with the help of the optical processing elements described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, state of matter (solid, liquid, gas, emulsion, mixtures thereof, etc.), and the like.

As used herein, the term "substance" or "sample," or variations thereof, refers to at least a portion of matter or material of interest to be tested or otherwise evaluated using the optical computing devices described herein. The substance includes the characteristic of interest, as defined above. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders, muds, glasses, mixtures, combinations thereof, and may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, treatment fluids, fracturing fluids, formation fluids, or any oilfield fluid, chemical, or substance commonly found in the oil and gas industry. In some cases, the substance may also refer to a solid material such as, but not limited to, rock formations, concrete, solid wellbore surfaces, pipes or flow lines, and solid surfaces of any wellbore tool or projectile (e.g., balls, darts, plugs, etc.).

As used herein, the term "electromagnetic radiation" refers to radio waves, microwave radiation, terahertz, infrared and near-infrared radiation, visible light, ultraviolet light, X-ray radiation and gamma ray radiation.

FIG. 1 is a schematic diagram of a logging-while-drilling environment 100 according to an illustrative embodiment. LWD may also be referred to as measurement-while-drilling (MWD). A drilling platform 5 is equipped with a derrick 10 that supports a hoist 15. A rig operator drills an oil or gas well for production or exploration using a string of drill pipes 20. The hoist 15 suspends a top drive 25 that rotates a drill string 20 as it lowers the drill string 20 through the wellhead 30. Connected to the lower end of the drill string 20 is a drill bit 35. The drill bit 35 is rotated and drilling is accomplished by rotating the drill string 20, by use of a downhole motor near the drill bit 35 or the top drive 25, or by both methods.

In one embodiment, recirculation equipment 40 pumps drilling mud or other fluids through a flow line 80 to the derrick 10. The flow line 80 goes up the derrick 10 and connects to a swivel 83 on the top drive through a stand pipe 81 and a flexible Kelly hose 82 to permit fluid to be pumped through the top drive 25 and into the drill string 20 below. The fluid is delivered down through the drill string 20 at high pressures and volumes to emerge through nozzles or jets in the drill bit 35. The drilling fluid then travels back up the hole via an annulus formed between the exterior of the drill string 20 and a borehole wall 50, through a blowout preventer (not illustrated) and a return line 45 into a retention pit 55, reservoir, or other enclosed receptacle(s) on the surface. On the surface, the drilling fluid may be cleaned and then recirculated by the recirculation equipment 40. The drilling fluid may be utilized to carry cuttings from the base of the bore to the surface and balance the hydrostatic pressure in the rock formations in the LWD environment 100.

A bottom hole assembly 60 (i.e., the lowermost part of drill string 20) may include thick-walled tubular elements called drill collars, which add weight, stability, and rigidity to aid the drilling process. The thick walls of these drill collars make them useful for housing instrumentation, tools, and LWD sensors. For example, in an embodiment, the bottom hole assembly 60 of FIG. 1 includes a sensor system 65 and a communications and control module 70. The sensor system 65 includes one or more integrated computational elements (ICE) along with necessary support circuitry 72. The one or more integrated computational elements along with the necessary support circuitry are referred to herein as the ICE module 72.

The ICE module 72 may enable the measurement of various chemical or physical properties of substances through the use of regression techniques. In one embodiment, an integrated computational element from the ICE module 72 may be formed with a substrate, e.g., an optically-transparent substrate having multiple stacked dielectric layers or films. In such stacks, each layer or film has a different refractive index from adjacent neighbors. While layers or films are referenced herein, it should be understood that the integrated computational element in the ICE module 72 is not an optical filter, but an optical processor. Sample electromagnetic radiation may be optically processed by the integrated computational element to isolate a spectrum specific to one or more chemical or physical properties of a substance. Specifically, the integrated computational element in the ICE module 72 may utilize reflection, refraction, interference, or a combination thereof to weight the sample electromagnetic radiation on a per-wavelength basis. This weighting process may produce an optical spectrum representative of the one or more chemical or physical properties of the downhole substance, which can then be utilized to determine the components of the downhole substance.

In an embodiment, the ICE module 72 may include one or more integrated computational elements. Each integrated computational element may operate on a predefined wavelength of the electromagnetic radiation (e.g., light), which has interacted with the downhole substance. Each integrated computational element has one or more corresponding support circuitries within the ICE module 72. The support circuitries may calculate intensities of electromagnetic radiation processed through their respective integrated computational elements to determine the one or more properties of the substance.

The accuracy of one or more determined properties of the substance can be improved by measuring a substance in close proximity to the substance's source. For example, a production fluid from a subterranean reservoir often contains hydrogen sulfide. If the production fluid is not close to the ICE module 72, the concentration of hydrogen sulfide may diminish due to uncontrolled diffusion into conveyance tubing. Thus, any compositionally-dependent properties determined at a point of measurement may not accurately represent those of the source.

A major factor that affects the proximity achieved to the substance's source is the support circuitry in the ICE module 72. The size of the support circuitry has a direct impact on the size of the probe containing the ICE module 72. Specifically, the bigger the support circuitry, the bigger the probe has to be to accommodate the size of the support circuitry, and therefore, the farther away it has to be placed from the substance's source. Consequently, decreasing the size of the support circuitry decreases the size of the probe, resulting in closer placement of the probe to the substance's source. Therefore, with a smaller probe, a more accurate measurement of the substance's properties is achieved.

In an embodiment, the support circuitry in the ICE module 72 may include components to detect light (i.e., light that has interacted with a substance and has been optically processed through respective integrated computational elements) and convert it into corresponding intensities. Specifically, the ICE module 72 may include a light to voltage converter to convert the light into corresponding voltage. The ICE module 72 may utilize a voltage to analog frequency converter to convert the voltage to corresponding analog frequency. As explained in further detail with reference to FIG. 3, the use of a voltage to analog frequency converter may reduce the size of the ICE module 72. An analog to digital frequency converter may be used in the ICE module 72 to convert the analog frequency to corresponding digital frequency. The digital frequency may then be converted into a corresponding intensity.

The sensor system 65 or bottom hole assembly 60 may also include, without limitation, a natural gamma ray detector, a resistivity tool, a nuclear magnetic resonance tool, a neutron porosity tool, or other exploration formation descriptor tools and sensors. Other tools and sensors may also be included in the bottom hole assembly 60 or sensor system 65, including, but not limited to, position sensors, orientation sensors, accelerometers, compasses, pressure sensors, temperature sensors, and vibration sensors.

From the various bottom hole assembly 60 sensors, the communications and control module 70 (telemetry module) may collect data regarding the formation properties or various drilling parameters, tool configurations and readings, and stores the data, for example in internal memory. In addition, some or all of the data may be transmitted to the surface by wireline communications, wireless communications, magnetic communications, seismic communications, or mud telemetry.

The communications signals may be received by a surface receiver 84, converted to an appropriate format, and processed into data by one or more computing or communications devices such as computer 75. Computer 75 may include a processor that executes software (which may be stored on portable information storage media 80, such as thumb drives, CDs, DVRs or installed computer memory, such as a hard disk, random access memory, magnetic RAM (MRAM) or other forms of non-volatile memory. The computer 75 may also receive user input via an input device 91, such as a keyboard, mouse pointer and mouse buttons, microphone, or other device to process and decode the received signals. The resulting sensory and telemetry data may be further analyzed and processed by computer 75 to generate a display of useful information on a computer monitor 90 or some other form of a display device or output, such as a mobile device like a hand held smart phone or a tablet PC. For example, a driller may employ the system of the LWD environment 100 to obtain and view information about downhole substances.

Figure 2:
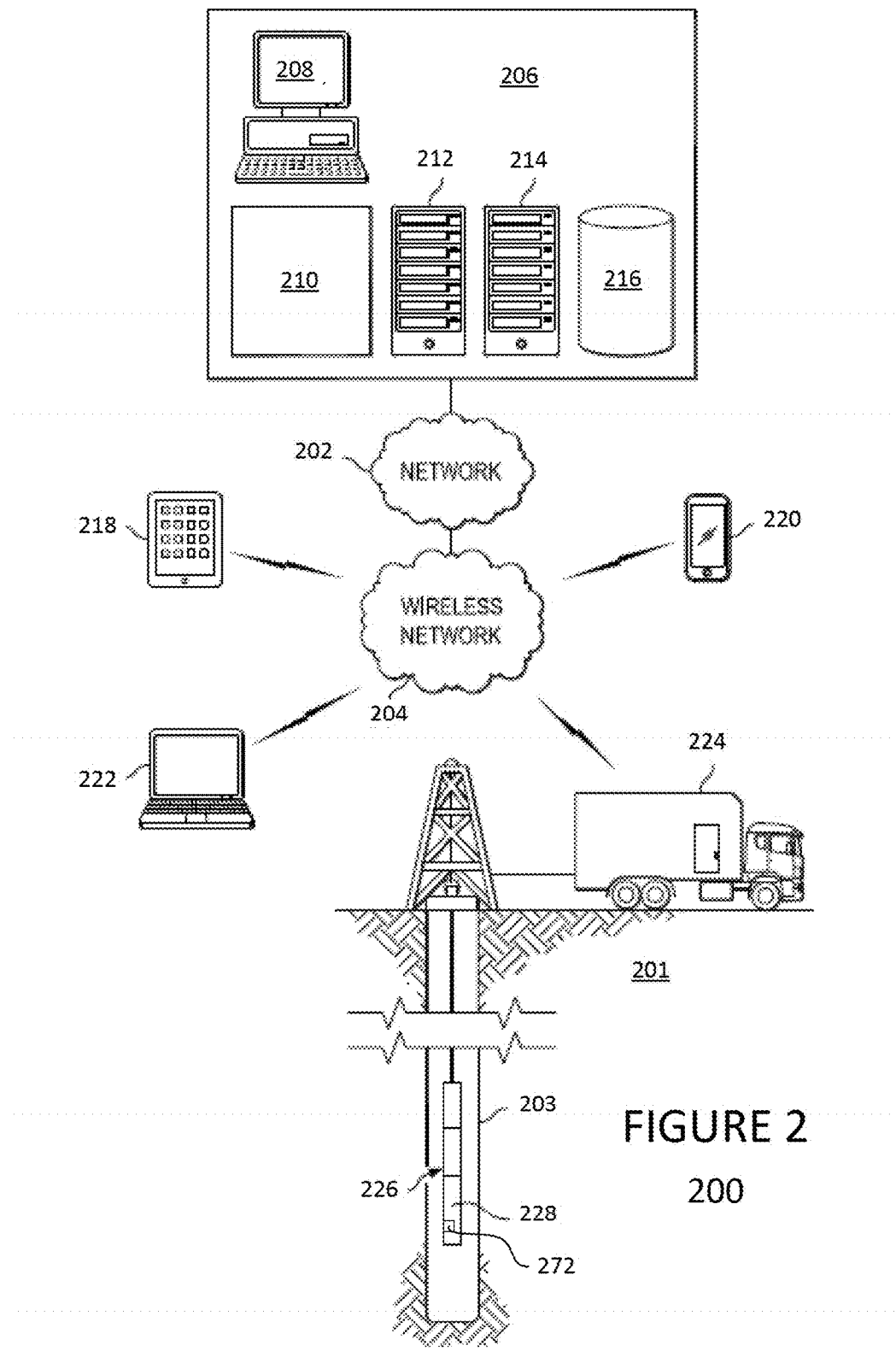
FIG. 2 is a schematic diagram of a logging environment according to an illustrative embodiment.

FIG. 2 is a schematic diagram of a logging environment 200 in accordance with an illustrative embodiment. The logging environment 200 may include any number of tools, devices, locations, systems, and equipment that may be utilized to provide the sensor tools, systems, and methods. The logging environment 200 may include a reservoir 201. The reservoir 201 is a designated area, location, or three-dimensional space that may include natural resources, such as crude oil, natural gas, or other hydrocarbons. The reservoir 201 may include any number of formations, surface conditions, environments, structures, or compositions. In an embodiment, sensors are utilized to determine properties and measurements of the reservoir 201 and a wellbore 203 penetrating the reservoir. For example, light sensors coupled to ICE module 272 are utilized to measure properties of substances in reservoir 201 and a wellbore 203 as described above with reference to FIG. 1. Processing or computations utilizing the substance properties may be performed downhole, on-site, off-site, at a movable location, at a headquarters, utilizing fixed computational devices, utilizing wireless devices, or over a data network using remote computers in real-time or offline processing.

The data and information determined from examination of the wellbore 203 may be utilized to perform measurements, analysis, or actions for exploration or production of the reservoir 201. The wellbore 203 may be drilled and configured with the reservoir 201 to extract wellbore fluids or gases from the formation. The size, shape, direction, and depth of the wellbore 203 may vary based on the conditions and estimated natural resources available. The wellbore 203 may include any number of support structures or materials, divergent paths, surface equipment, or so forth.

In one embodiment, the processes described herein may be performed utilizing specialized sensor tools, including optical sensors (such as optical sensors coupled with ICE module 272), reluctance sensors, induction proximity sensors, resistivity sensors, magnetic field sensors, acoustic proximity sensors, location sensors (e.g., that permit the measurement of a distance or direction to a manmade subterranean structure), orientation sensors (e.g., gyroscopes, compasses, accelerometers, etc.), logic, interconnects, power sources, and other similar electrical components. The logic utilized by the tools may include processors, controllers, memories, field programmable gate arrays (FPGAs), batteries, wires, leads, pins, connectors, amplifiers, application specific integrated circuits, computer instructions, code, programs, or applications, or any combination of software, hardware, and firmware.

In one embodiment, the logging environment 200 may include a network 202, a wireless network 204, a facility 206, a personal computer 208, a management system 210, servers 212 and 214, a database 216, a tablet 218, a wireless device 220, a laptop 222, and a mobile computing system 224. The mobile computing system 224 may include downhole equipment 226 and tool 228. The tool 228 includes a sensor system with an ICE module 272.

In an embodiment, the support circuitry in the ICE module 272 may include components to detect light (i.e., light that has interacted with a substance and has been optically processed through respective integrated computational elements) and convert it into corresponding intensities. Specifically, the ICE module 272 may include a light to voltage converter to convert the light into corresponding voltage. The ICE module 272 may utilize a voltage to analog frequency converter to convert the voltage to corresponding analog frequency. The use of a voltage to analog frequency converter reduces the size of the ICE module 272. An analog to digital frequency converter may be used in the ICE module 272 to convert the analog frequency to corresponding digital frequency. The digital frequency is then converted into a corresponding intensity.

The network 202 may be any type of computing or communications network including one or more of the following networks: a wide area network, a local area network, one or more private networks, Internet or public networks, a telephone network (e.g., publicly switched telephone network), a cable network, a satellite network, one or more cellular networks, cloud networks, virtual networks, and other wireless and data networks.

The wireless network 204 is one example of a wireless network for regional or local communications (e.g., WiFi, GMS, 4G, LTE, PCS, Bluetooth, Zigbee, WiMAX, GPRS, etc.). The network 202 and the wireless network 204 may include any number of network nodes, devices, systems, equipment, and components (not depicted), such as routers, servers, network access points/gateways, cards, lines, wires, switches, DNS servers, proxy servers, web servers, and other network nodes and devices for assisting in routing and computation of data/communications as herein described.

In another embodiment, integrated or external tools or components communicating with the mobile computing system 224 may be configured to penetrate an earth formation through the wellbore 203 to stimulate, energize, and measure parameters of a formation or a nearby man made structure. One or more sensors or logging tools (e.g., probes, drill string measurement devices, nuclear magnetic resonance imagers, etc.) may be integrated with or connected to the downhole equipment 226 and tool 228 communicating with mobile computing system 224 to perform signal generation, measurements, logging, data retrieval, data storage, processing, and information display.

For example, the mobile computing system 224 may determine any number of static and dynamic properties of the reservoir 201. The static and dynamic properties may include measurements of or changes in composition (e.g., physical/chemical fluid composition, hydrocarbon composition levels, measurements, and statistics), pressure, wellbore distances and diameters, ranges, depth, temperature, fluid flow rate, density, porosity, position and displacement, depth, and so forth. Properties of substances within the reservoir 201 or wellbore 203 may be measured using tool 228 and may be utilized to make any number of determinations regarding the substances within the reservoir 201.

For example, at various times during the drilling process, a drill string (see FIG. 1) may be removed from the borehole 203. Once the drill string has been removed, logging operations may be conducted using the tool 228 which may be a wireline or wireless tool. For example, the tool 228 may be a sensing instrument suspended by a cable having conductors for transporting power to the tool and telemetry from the tool to the surface. The tool 228 may be preconfigured for testing or configured in real-time for the conditions of the logging environment. The tool 228 may be configured to operate with or without rotation.

The tool 228 may alternatively represent any number of LWD, MWD, seismic-while-drilling (SWD), or other downhole or reservoir tools. In one embodiment, the tool 228 may rotate one or more sensors to enhance measurements made by the tool 228. The tool 228 may store or communicate the signals and data generated as measured by changes in light to determine properties of substances in each section of the reservoir 201 or the wellbore 203. The tool 228 may be self-contained and powered or connected to one or more fixed or mobile stations, systems, devices, equipment, or vehicles at the surface.

In one embodiment, the tool 228 or other portions of the mobile computing system 224 may communicate optically processed information, such as measurements from integrated computational elements 272, from the tool 228. The personal computer 208, tablet 218, wireless device 220, laptop 222, and mobile computing system 224 may execute a local program or application (app) to configure the tool 228 and retrieve and utilize the measurements acquired in the processes described herein. For example, the wireless device 220 may be configured to increase or decrease the voltage, frequency, amplitude, sensitivity, or other parameters utilized by the tool 228. The tool 228 may also be configured with programs or algorithms for self-configuration based on applicable environments, parameters, conditions, or so forth. The wireless device 220 may also be utilized to filter particular types of fields, turn the tool (in any of three dimensions), or so forth.

In another embodiment, the computations and analysis of the data read by the tool 228 may be performed by management system 210, servers 212 and 214, or other network devices. For example, the user may submit information and parameters utilizing the wireless device 220 to perform the calculations on the server 212 with the results being stored in database 216 for subsequent access. The database 216 may store the depths and locations of components, sensor orientation information, casing thicknesses, static properties, dynamic properties, parameters, configuration, settings, and so forth. The database 216 may be accessed by any number of users and devices in the logging environment 200 to retrieve and update the data.

In one embodiment, the servers 212 and 214 may execute an application that is available to any of the devices of the logging environment 200 through the network 202 and the wireless network 204. For example, the application may display a user interface for receiving parameters, properties, and other information for configuring the tool 228 or reviewing the measurements of the tool 228. In one embodiment, the server 214 is a Web server that hosts the application for downhole measurement processing that is accessible through one or more browsers utilized by any of the personal computer 208, tablet 218, wireless device 220, laptop 222, and mobile computing system 224.

Figure 3:
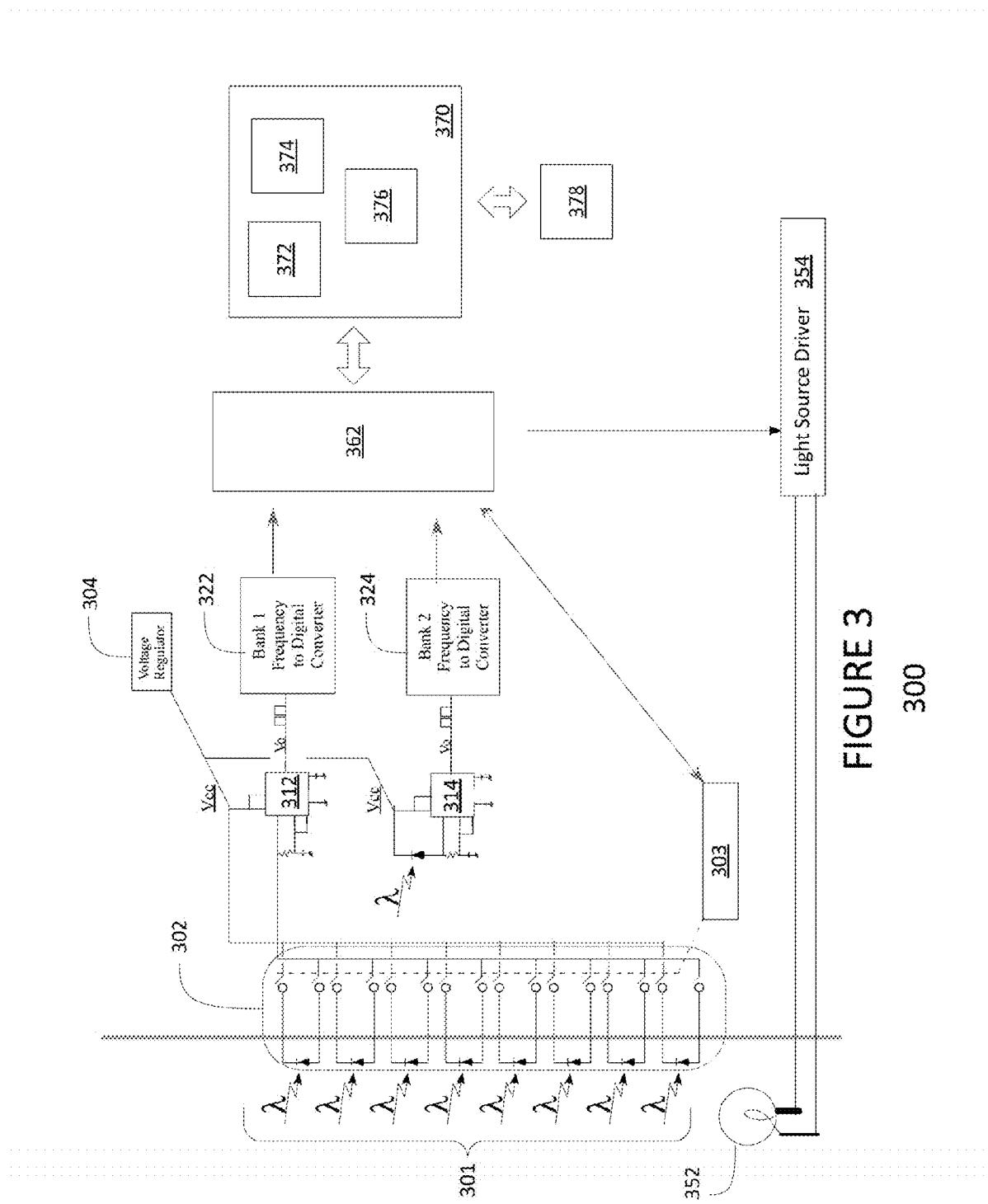
FIG. 3 is a block diagram of a system to convert light into intensity according to an illustrative embodiment.

With reference to FIG. 3, in conventional downhole systems utilizing integrated computational elements, the light interacting with a substance is converted into voltage and this voltage is amplified by a series of amplifiers. The amplified voltage is then measured and a corresponding intensity of the light is calculated. From the intensity, one or more properties of the substance may be determined. One of the problems with this approach is that the voltage has to be significantly amplified to calculate a corresponding intensity. To do so, multiple amplifiers have to be utilized in a downhole environment due to the high temperatures in downhole surroundings (for example, 200° C. or higher). More particularly, the amplification voltage range that can be achieved by a single amplifier is smaller at higher temperatures than lower temperatures. Thus, multiple amplifiers have to be utilized to amplify the voltage, resulting in complicated and relatively large circuitry.

To alleviate the problems above, in an embodiment illustrated by FIG. 3, the light interacting with a substance may be converted into corresponding voltage and this voltage may be converted into the frequency domain and then ultimately converted into corresponding intensities. By converting the voltage signals into the frequency domain, the degree of amplification of such signals may be reduced. Consequently, compared to conventional systems, less voltage amplification may be required, reducing the need for multiple amplifiers or larger or multistage amplifiers, thereby resulting in less support circuitry. This may lead to smaller circuits and systems that are more accurate in high temperature environments. More particularly, FIG. 3 illustrates a system 300, such as an optical computational system, to convert light into digital frequency according to an illustrative embodiment. In an embodiment, the system shown in FIG. 3 is the support circuitry incorporated into an ICE module (e.g., ICE module 72 or 272) in a downhole environment.

In an embodiment, system 300 may include a light to voltage converter 302, a converter switching module 303, a voltage regulator 304, voltage to analog frequency converters 312 and 314, analog to digital frequency converters 322 and 324, controller module 362, light source 352, and light source driver 354. System 300 may be connected to intensity module 370. Intensity module 370 may be a digital frequency to intensity converter.

The light to voltage converter 302 may convert light into voltage. The converter switching module 303 may control the operation of the light to voltage converter 302 by switching the light to voltage converter 302 on or off. In an embodiment, the light to voltage converter 302 may be a thermopile detector array with multiple channels. Each channel may be a thermocouple that detects light and outputs corresponding voltages. In another embodiment, the light to voltage converter 302 may be an optical transducer array, such as a photodiode detector array, with multiple channels. As used herein, photodiodes are exemplary optical transducers. Descriptions of photodiodes are intended to encompass other optical transducers as well. Each channel is an optical transducer that detects light and outputs corresponding voltages. Alternatively, any other suitable device or array of devices may be utilized to detect light and generate a voltage indicative of the light detected.

The voltage to analog frequency converters 312 and 314 may convert voltage to corresponding analog frequencies. In an embodiment, the voltage to analog frequency converters 312 and 314 include one or more voltage to frequency converters (VFCs). In another embodiment, the voltage to analog frequency converters 312 and 314 include one or more voltage controlled oscillators (VCOs). Alternatively, any other suitable device or array of devices may be utilized to convert a voltage signal into a frequency signal.

Voltage regulator 304 may regulate input voltage. In an embodiment, the voltage regulator may amplify the input voltage. Allowing a controller module 362 to control voltage regulator 304 can implement a variable gain. In one embodiment, the voltage regulator 304 may be a linear regulator. In embodiments, the voltage regulator 304 may be a linear regulator. In various embodiments, the voltage regulator 304 may include a switching regulator or a combination (hybrid) regulator. Alternatively, any other suitable device or array of devices may be utilized to regulate and amplify the voltage output from light to voltage converter 302.

The analog to digital frequency converters 322 and 324 may convert input analog frequency to corresponding digital frequency. In an embodiment, the analog to digital frequency converters 322 and 324 may be pulse counters that count the number of pulses received from the voltage to analog frequency converters 312 and 314 that occur in a fixed time period, which is proportional to the voltage input of voltage to analog frequency converters 312 and 314. In another embodiment, analog to digital frequency converters 322 and 324 may be period timers that determine the period of the output frequency of analog frequency converters 312 and 314. Alternatively, analog to digital frequency converters 322 and 324 may be any other suitable device for converting an analog frequency into a digital value representative of such analog frequency.

Light source 352 may generate light. In one embodiment, light source 352 may be a pulsed light source. In an alternate embodiment, light 352 may be a non-pulsed (continuous) light source. Light source 352 may be a full spectrum light source, a broad-spectrum light source, or a narrow spectrum light source such as an ultraviolet light source or an infrared light source. The operation of the light source 352 is controlled by the light source driver 354. The light source driver 354 turns the light source 352 on or off.

Controller module 362 may control one or more operations of system 300. In an embodiment, controller module 362 may be a microcontroller. In an alternative embodiment, controller module 362 may be a microprocessor. Controller module 362 may control the operation of the converter switching module 303 and thus controls the operation of light to voltage converter 302. Controller module 362 may also control the timing of the light source driver 354, and therefore controls the timing of when the light source 352 is turned on or off. Controller module 362 may reduce and scale the data received from the analog to digital frequency converters 322 and 324. In an embodiment, the controller module 362 may also control communication with intensity module 370.

Intensity module 370 may convert digital frequencies to corresponding intensities of light detected by light to voltage converter 302. In an embodiment, intensity module 370 may include a processor 372 and a memory 374. Alternatively, intensity module 370 may be implemented as a microcontroller. Processor 372 executes instructions stored in the memory 374. The memory 374 may include random access memory (RAM), magnetic RAM (MRAM), and other forms of non-volatile memory. In an embodiment, memory 374 may include instructions to convert scaled digital frequencies to corresponding intensities. In an embodiment, intensity module 370 may include data storage 376. Data storage 376 may be a static memory device. In an embodiment, processor 372 may store information pertaining to intensities on data storage 376.

In an embodiment, characteristics determination module 378 may include a processor and a memory as described with reference to intensity module 370. Alternatively, characteristics determination module 378 may be implemented as a microcontroller. Characteristics determination module 378 may utilize one or more intensities associated with a substance to determine the characteristics of the substance in an environment. For example, the one or more intensities may be utilized to determine the presence or concentration of a substance in fluid extracted from a downhole formation. In an exemplary embodiment, light may interact with a substance and this light is optically processed by a particular integrated computational element programmed to recognize the optical footprint of a specific substance, which is a constituent of the substance, such as methane, ethane, propane, aromatics, saturates, or water. Once the existence of the specific substance is determined by the integrated computational element, the optically processed light may be converted into a corresponding intensity. This corresponding intensity may be utilized by the characteristics determination module 378 to determine the concentration of the specific substance within a downhole formation.

In one embodiment, intensity module 370 or characteristics determination module 378 may be implemented in a remote system. In other embodiments, the operations of intensity module 370 and characteristics determination module 378 may be performed locally. For example, the components of system 300, intensity module 370, and characteristics determination module 378 may be integrated into controller module 362 and may be located on the same chip. In an embodiment, intensity module 370 and characteristics determination module 378 may be implemented as field programmable gate arrays (FPGAs) or application-specific integrated circuits (ASICs).

In operation, the controller module 362 may send a signal to light source driver 354 to turn on the light source 352. In response, the light source driver 354 may switch on the light source 352 and light may be generated by the light source 352. The light from the light source 352 may interact with a substance (not shown). This light, which has interacted with the substance, may be optically processed by an integrated computational element in an ICE module (e.g., ICE module 72 or 272) and the resulting light may be light 301. The controller module 362 may send a signal to the converter switching module 303 to turn on the light to voltage converter 302. Light 301 may be detected and converted into corresponding voltage by the light to voltage converter 302. The voltage may be multiplexed and transmitted to the voltage to analog frequency converter 312. In an embodiment, the voltage regulator 304 may regulate the voltage level. The voltage to analog frequency converter 312 may convert the voltage to corresponding analog frequency. In an alternate embodiment, if the light to voltage converter 302 includes multiple banks, multiple voltage to frequency converters 312, 314 may be utilized as explained below. The analog frequency is transmitted to the analog to digital frequency converter 322. The analog to digital frequency converter 322 may convert the analog frequency into a corresponding digital frequency. The digital frequency may then be transmitted to the intensity module 370, which converts the digital frequency into corresponding intensity. The corresponding intensity may be utilized by the characteristics determination module 378 to determine characteristics of the downhole substance.

An interface utilized to communicate to the intensity module 370 may utilize a controller area network (CAN), 1553 (a standard for serial transmission of data), RS232 (a standard for serial transmission of data), serial peripheral interface (SPI), or RS485 (a standard for data transmission that can span relatively large distances (up to 4,000 feet)) protocols.

In one embodiment, the light to voltage converter may include multiple banks. For example, a color sensing photodiode detector array can include four banks: red, green, blue filters with the final bank left unfiltered. In an embodiment, if the light to voltage converter includes multiple banks—for example, two banks—system 300 may include two corresponding voltage to frequency converters 312, 314. Each voltage to analog frequency converter 314 and 314 transmits respective analog frequencies to the corresponding analog to digital frequency converters 322, 324.

Figure 4:
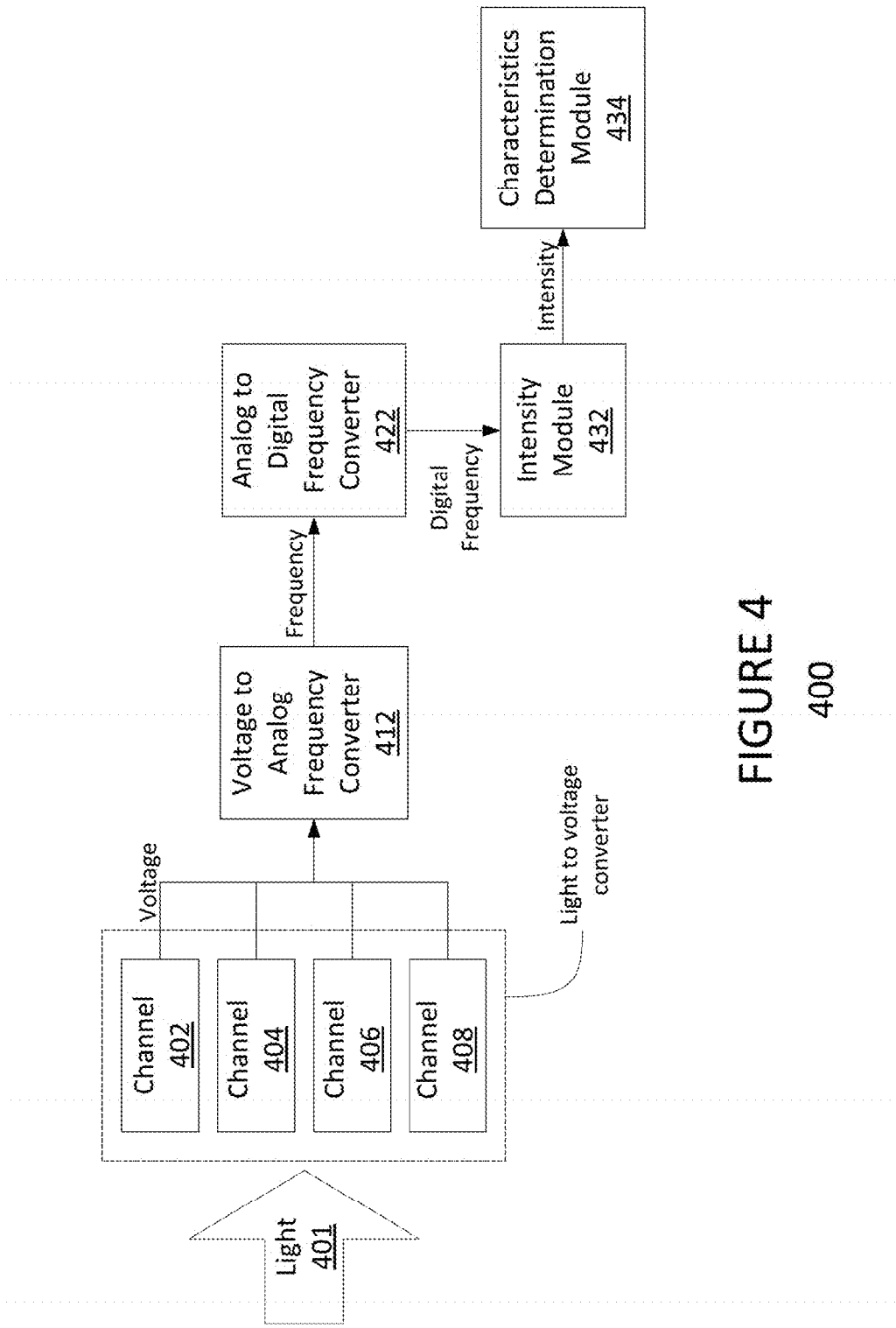
FIG. 4 is a block diagram of a system to convert light into intensity according to an illustrative embodiment.

FIG. 4 is a block diagram of a system 400 to convert light into intensity according to an illustrative embodiment. In an embodiment, system 400 is the support circuitry incorporated into an ICE module (e.g., ICE module 72 or 272) used in a downhole environment.

In an embodiment, system 400 may include light to voltage converter channels 402, 404, 406, and 408, voltage to analog frequency converter 412, analog to digital frequency converter 422, a digital frequency to intensity converter 432, and a characteristics determination module 434. In an embodiment, the digital frequency to intensity converter 432 is part of a separate system (e.g., intensity module 370 from FIG. 3).

Figure 5:
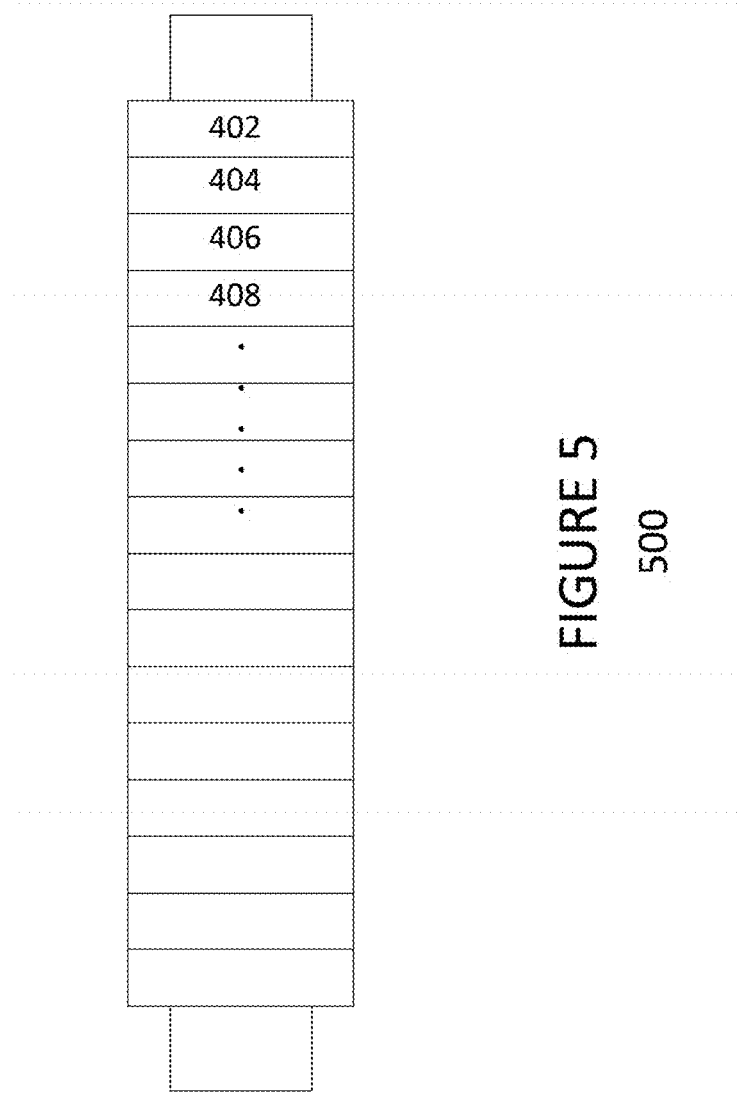
FIG. 5 is a schematic diagram of a light to voltage converter according to an illustrative embodiment.

In an embodiment, the one or more light to voltage converter channels 402-408 are part of a light to voltage converter 500 as shown in FIG. 5. In an embodiment, the light to voltage converter 500 is a thermopile detector array with multiple channels. Each channel, for example, channels 402-408, may detect light and output corresponding voltages. In such an embodiment, each channel 402-408 may be a thermocouple. In another embodiment, the light to voltage converter 500 may be a photodiode detector array with multiple channels. In such an embodiment, each channel 402-408 may be a photodiode. Alternatively, the light to voltage converter 500 may be any other suitable device or array of devices to detect light and generate a voltage indicative of the light detected. Although FIG. 5 shows the light to voltage converter 500 as having sixteen channels for conciseness and clarity purposes, a person having ordinary skill in the art will appreciate that the light to voltage converter 500 may include any number of channels based on the context of its use including, without limitation, 32, 64, or 128 channels.

Figure 6:
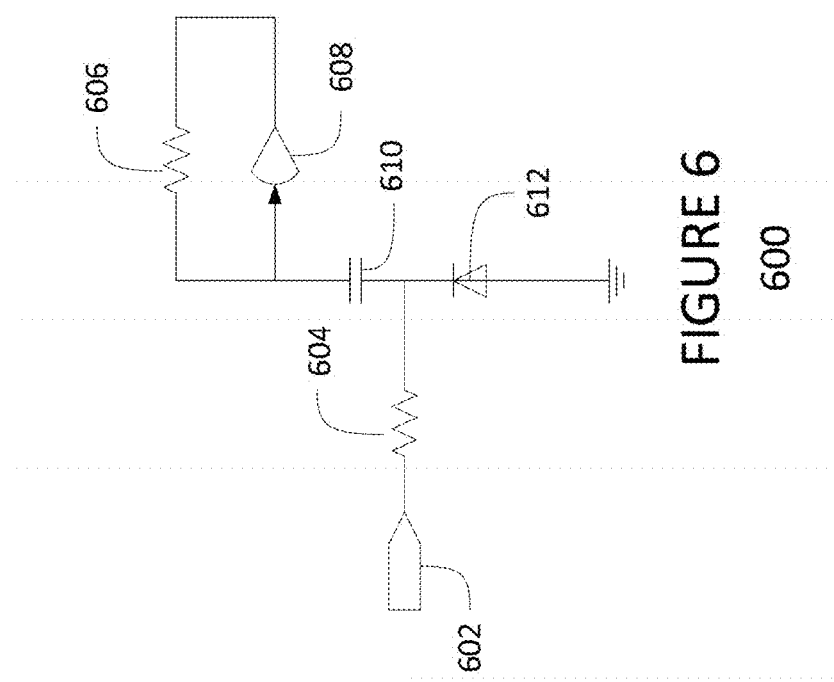
FIG. 6 is a circuit diagram of a voltage controlled oscillator according to an illustrative embodiment.

Returning to FIG. 4, the voltage to analog frequency converter 412 may convert voltage to corresponding analog frequencies. In an embodiment, the voltage to analog frequency converter may include one or more voltage to frequency converters (VFCs). In another embodiment, the voltage to analog frequency converter 412 may include one or more voltage controlled oscillators (VCOs). Alternatively, the voltage to analog frequency converter 412 may include any other suitable device or array of devices to convert a voltage signal into a frequency signal. FIG. 6 shows a circuit diagram of a VCO 600 according to an illustrative embodiment. The VCO 600 may receive voltage 602 as input and converts this input voltage into corresponding analog frequency. The VCO 600 may include one or more resistors 604, 606, capacitors 610, operational amplifiers 608, and diodes 612 connected in a serial or parallel fashion. The circuit shown in FIG. 6 is exemplary and a person having ordinary skill in the art will appreciate that a VCO may be implemented using various other types of circuits.

Figure 7:
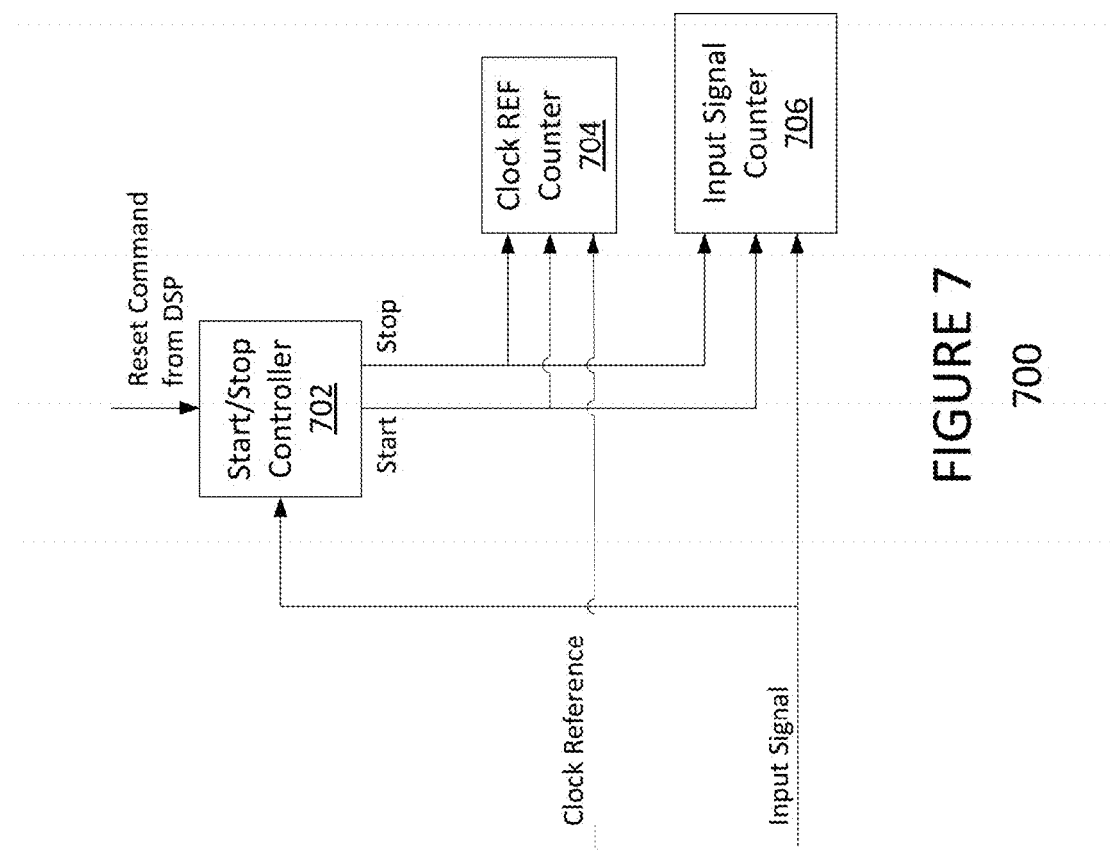
FIG. 7 is a block diagram of a digital frequency counter according to an illustrative embodiment.

Returning to FIG. 4, the analog to digital frequency converter 422 may convert input analog frequency to corresponding digital frequency. In an embodiment, the analog to digital frequency converter 422 may include one or more digital frequency counters. Alternatively, the analog to digital frequency converter 422 may include any other suitable device or array of devices to convert an input analog frequency to corresponding digital frequency. A block diagram of a digital frequency counter 700 is shown in FIG. 7 according to an illustrative embodiment. The digital frequency counter 700 may include an input signal counter 706 to receive an input analog frequency, a clock reference counter 704 to count a clock reference, and a controller 702 to control the operations of the input signal counter 706 and the clock reference counter 704. The digital frequency counter 700 may receive as input a clock reference and an analog frequency. The clock reference is received by the clock reference counter 704 and the input analog frequency is received by the input signal counter 706. The controller 702 may control the operation of the counters 704 and 706 by sending start and stop signals. In an embodiment, the digital frequency may be calculated by the following equation: digital frequency value=clock reference×(clock reference counter value/input signal counter value). The circuit topology shown in FIG. 7 is exemplary and a person having ordinary skill in the art will appreciate that in other embodiments, different digital frequency counters may be utilized.

Returning to FIG. 4, the digital frequency to intensity converter 432 may convert digital frequency into a corresponding intensity. As discussed with reference to intensity module 370 of FIG. 3, in one embodiment, the digital frequency to intensity converter 432 may include a processor (not shown) and a memory (not shown). The processor executes instructions stored in the memory. In an embodiment, memory may include instructions to convert digital frequencies to corresponding intensities. In an embodiment, the processor may store information pertaining to intensities on the data storage. In an embodiment, the digital frequency to intensity converter 432 may be part of the system 400. For example, the components of the digital frequency to intensity converter 432 and the rest of the components of system 400 may be located on the same chip. In another embodiment, the digital frequency to intensity converter 432 may be a separate system from system 400.

Characteristics determination module 434 may utilize one or more intensities determined by intensity converter 432 to determine the characteristics of a substance in a downhole environment. For example, the one or more intensities may be utilized to determine the presence or concentration of a substance in fluid extracted from a downhole formation. Characteristics determination module 434 may be implemented in a similar manner to characteristics determination module 378 of FIG. 3.

In operation, light from a light source may interact with a substance (not shown). This light, which has interacted with the substance, may be optically processed by an integrated computational element in an ICE module (e.g., ICE module 72 or 272) and the resulting light is light 401. Light 401 may be detected and converted into voltage by the one or more light to voltage converter channels 402-408. The output voltage from these channels 402-408 i may be s multiplexed and transmitted to the voltage to analog frequency converter 412. In an embodiment, the voltage output from channels 402-408 may be optionally amplified prior to transmission to the frequency converter 412. The voltage to analog frequency converter 412 may convert the input voltage into corresponding analog frequency. The analog frequency may be then converted into corresponding digital frequency by the analog to digital frequency converter 422. The digital frequency to intensity converter 432 may process the digital frequency and may convert it into corresponding intensity. The corresponding intensity may be utilized by the characteristics determination module 434 to determine characteristics of the substance.

Figure 8:
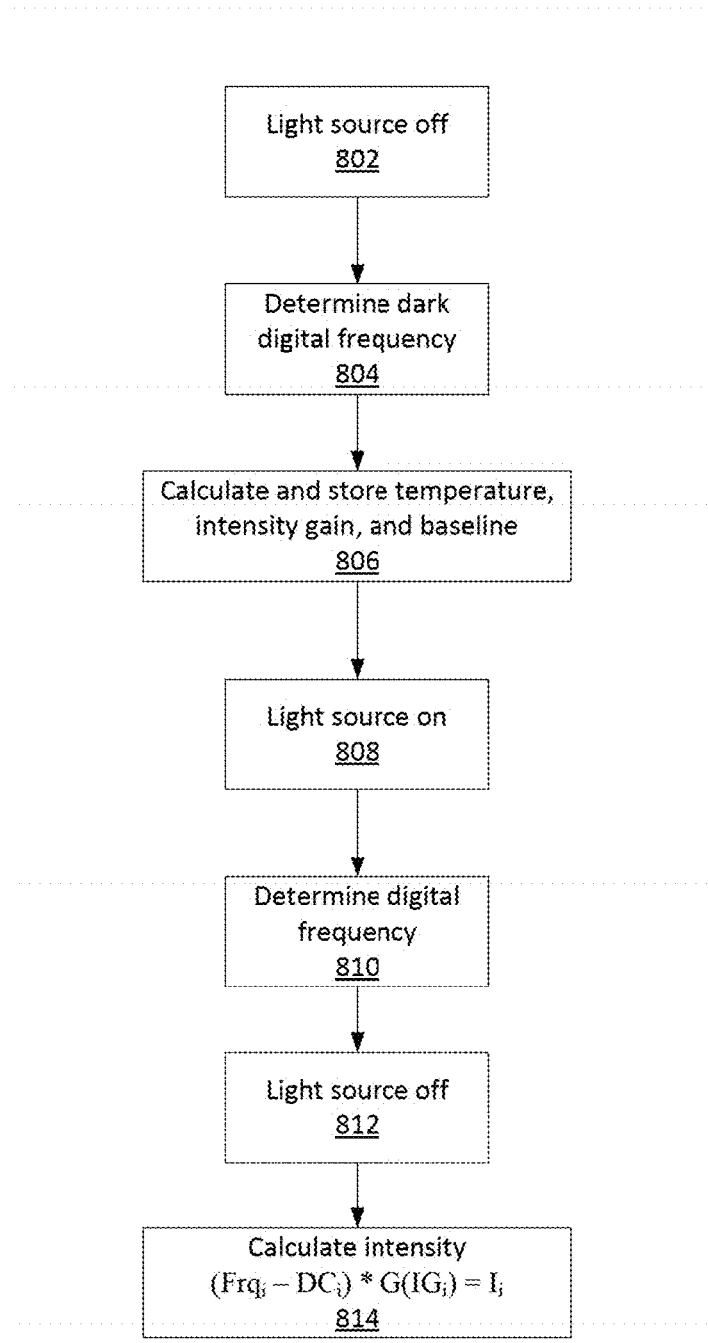
FIG. 8 is a flowchart of a process to calculate intensity from a light source according to an illustrative embodiment.

FIG. 8 is a flowchart of one embodiment of a process 800 to calculate the intensity of light received from a downhole formation illuminated by a light source. The light may be optically processed by one or more integrated computational elements and the resulting "processed" light may be detected and the intensity of such light may be determined.

For semiconductor based detectors, note that resistance based sensors are similar, the signal generated with no optical input may be a function of the semiconductors band gap and temperature. This may be measured through the instrument train as at Frequency representing the "dark current" for the detector, represented as Freq(lite off).

It turns out for many system the optical gain of the detector system is a function of temperature, so the dark current may be used in two different places (Raw intensity detector response (Frq (lit)−Frq(Dark)) and in setting the temperature dependent gain of the detector system, which may be a function or calibration table G(GI), which may be expressed as a temperature correcting the system gain (also converts values from frequency to intensity), represented as Gain(Freq(lite off)). Thus, $I$=(Freq(lite on)−Freq(lite off))*Gain(Freq(lite off))

(Intensity I corrected=Raw intensity*correction for detector efficiency with temperature)

The gain function can be used to hide conversion factors and scaling parameters, the gain function need not be linear. The table form can be used to place 0 into the gain function where the detector response is unreliable or unstable.

In response to a trigger signal, a light source may be turned off at step 802. A dark digital frequency (i.e., a digital frequency of light detected when the light source is turned off) corresponding to measurements at one or more channels of a light to voltage converter may be determined at step 804. For each channel, based on the dark digital frequency, a corresponding temperature, intensity gain, and baseline may be calculated at step 806. The values calculated during the dark cycle, such as the dark digital frequency, may be utilized to account for any minimal amount of light that exists in a downhole environment. These dark cycle variable values may be used as offsets when calculating intensity as shown in the equation below. The light source may be turned on at step 808. The light may interact with one or more substances and may be processed by one or more integrated computational elements. A digital frequency corresponding to the ICE processed light detected at one or more channels of the light to voltage converter may be determined at step 810. As described previously, in an embodiment, to calculate the digital frequency (or dark digital frequency), light detected at each channel of a light to voltage converter may be converted to corresponding voltage. The voltage may be converted to corresponding analog frequency. The analog frequency may be then converted to corresponding digital frequency. This digital frequency may be used to calculate the intensity.

Optionally, at step 812, to conserve resources, the light source may be turned off. For each channel, based on the frequency, a corresponding intensity may be calculated at step 814. In an embodiment, to determine intensity, the following equation may be utilized: $(Frq_i - DC_i)*G(IG_i)=I_i$. Here, $Frq_i$ is the digital frequency measured from channel i, $DC_i$ is the dark digital frequency measured from channel i, G is a corrective gain factor and $IG_i$ is the intensity gain measured from channel i.

Figure 9:
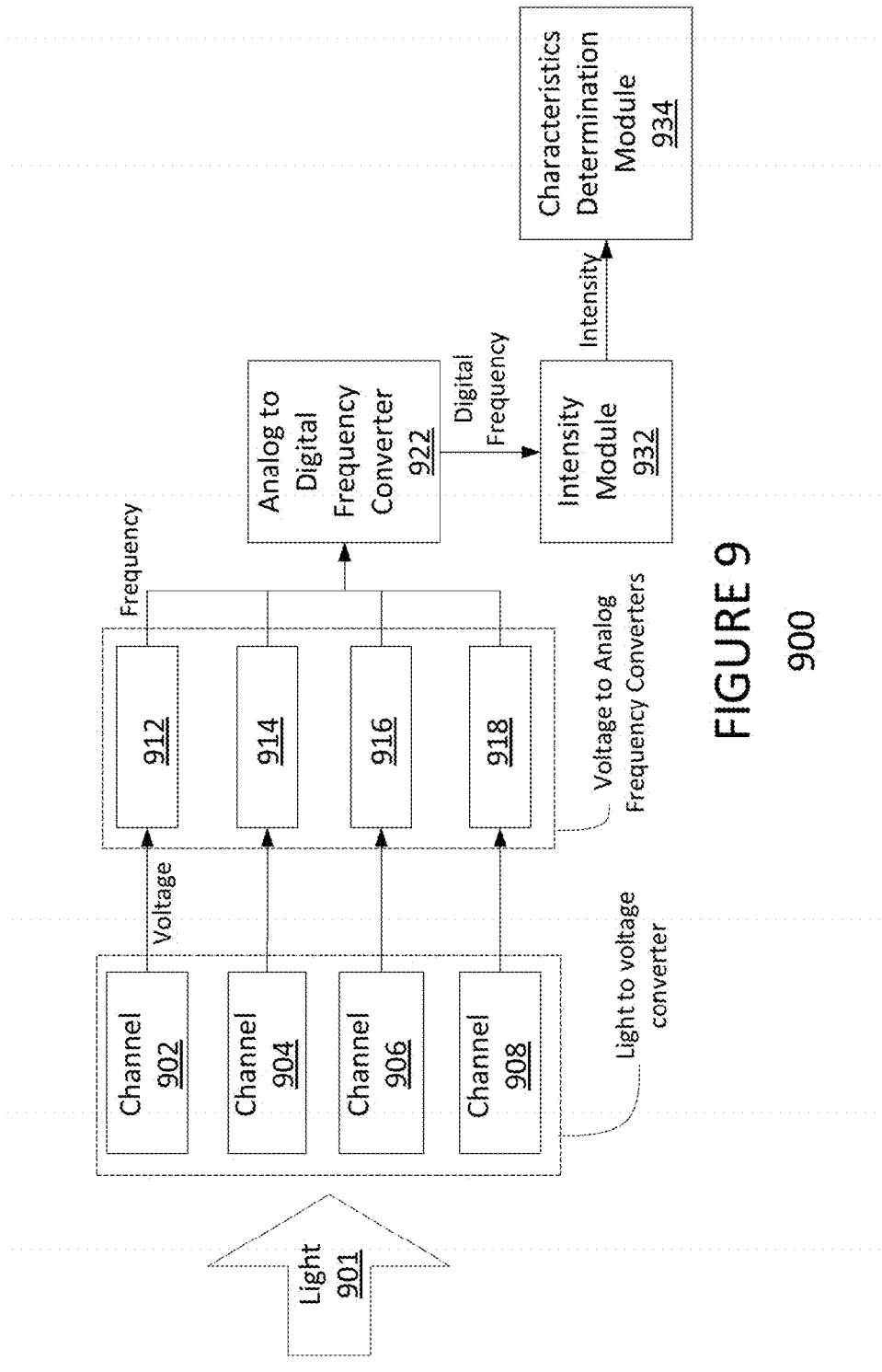
FIG. 9 is a block diagram of a system to convert light into intensity according to an illustrative embodiment.

Although FIG. 3 and FIG. 4 show that the multiplexing occurs at the point when light is converted to voltage, in other embodiments the multiplexing may occur at other points of the process. For example, FIG. 9 is a block diagram of a system 900 where the multiplexing occurs after the voltage is converted to analog frequency according to an illustrative embodiment. Light 901 may be detected and converted into voltage by one or more light to voltage converters 902-908. The output voltage from these converters 902-908 may be transmitted to respective voltage to analog frequency converters 912-918. In an embodiment, the voltage output from converters 902-908 may be optionally amplified prior to transmission to analog frequency converters 912-918. The voltage to analog frequency converters 912-918 may convert the respective voltage into corresponding analog frequencies. The analog frequencies may then be multiplexed and transmitted to an analog to digital frequency converter 922. The analog to digital frequency converter 922 may convert the multiplexed analog frequency to a digital frequency. Digital frequency to intensity converter 932 may process the digital frequency and may convert it into corresponding intensity profile as explained in process 800 above. The corresponding intensity profile may be utilized by a characteristics determination module 934 to determine characteristics of the downhole substance. One or more intensities may be utilized in each of the various embodiments described herein. In another embodiment, the multiplexing occurs after each digital frequency corresponding to each channel is determined. That is, the digital frequencies corresponding to each channel may be multiplexed and the multiplexed digital frequency may be transmitted to the system 932.

The circuits described in the embodiments above may be implemented as one or more application-specific integrated circuits (ASICs), field programmable gate arrays (FPGAs), complex programmable logic devices (CPLDs), or other hybrid assemblies. In certain embodiments, one or more of the circuits are fabricated using silicon on sapphire (SOS) or silicon on insulator (SOI) processes. Such processes ensure proper functioning of the circuits in hostile temperatures (e.g., temperatures above 200° C.).

In addition to the embodiments described above, many examples of specific combinations are within the scope of the disclosure, some of which are detailed below.

EXAMPLE 1

An optical computational system to determine characteristics of a substance, the system comprising:

at least one integrated computational element (ICE) module housed within the system, the at least one ICE module being placed proximate to the substance to determine at least one characteristic of the substance, the at least one ICE module comprising:

an integrated computational element that optically processes electromagnetic radiation, wherein the electromagnetic radiation has previously interacted with the substance, an electromagnetic radiation to voltage converter that detects the processed electromagnetic radiation using at least one channel of the electromagnetic radiation to voltage converter and further converts the detected electromagnetic radiation into at least one voltage, a voltage to analog frequency converter that converts the at least one voltage into at least one analog frequency, an analog to digital frequency converter that converts the at least one analog frequency into at least one digital frequency, and a processor operable to:

determine at least one intensity from the at least one digital frequency, and determine the at least one characteristic of the substance in response to the determined at least one intensity profile.

EXAMPLE 2

The system of example 1, the system further comprising a multiplexer to multiplex the at least one voltage prior to converting the at least one voltage into the at least one analog frequency.

EXAMPLE 3

The system of example 1, the system further comprising a multiplexer to multiplex the at least one analog frequency prior to converting the at least one analog frequency into the at least one digital frequency.

EXAMPLE 4

The system of example 1, the system further comprising a multiplexer to multiplex the at least one digital frequency prior to determining the at least one intensity.

EXAMPLE 5

The system of example 1, wherein the electromagnetic radiation to voltage converter is a thermopile detector array and each channel is a thermocouple.

EXAMPLE 6

The system of example 1, wherein the electromagnetic radiation to voltage converter is a photodiode detector array and each channel is a photodiode.

EXAMPLE 7

The system of example 1, wherein the at least one voltage to analog frequency converter comprises a voltage controlled oscillator.

EXAMPLE 8

The system of example 1, wherein to determine the least one intensity from the at least one digital frequency, the processor is further configured to:

determine at least one dark frequency, wherein the at least one dark frequency is determined with an electromagnetic radiation source turned off, calculate at least one intensity gain based on the at least one dark frequency, determine the at least one digital frequency with the electromagnetic radiation source on, and determine the at least one intensity based on the at least one digital frequency, the at least one dark frequency, and the at least one intensity gain.

EXAMPLE 9

The system of example 1, wherein at least one of the electromagnetic radiation to voltage converter, the voltage to analog frequency converter, and the analog to digital frequency converter comprises an application-specific integrated circuit.

EXAMPLE 10

The system of example 1, wherein the processor is further operable to determine a concentration of the at least one characteristic.

EXAMPLE 11

The system of example 1, wherein at least one of the electromagnetic radiation to voltage converter, the voltage to analog frequency converter, and the analog to digital frequency converter comprises a circuit fabricated using at least one of a silicon on sapphire process and a silicon on insulator process.

EXAMPLE 12

A method to determine at least one characteristic of a substance, the method comprising:

placing at least one integrated computational element (ICE) module proximate to the substance, wherein the at least one ICE module is housed within a tool;

processing, by an integrated computational element in the ICE module, electromagnetic radiation, wherein the electromagnetic radiation has previously interacted with the substance;

detecting the processed electromagnetic radiation by at least one channel of a electromagnetic radiation to voltage converter in the ICE module;

converting the detected electromagnetic radiation into at least one voltage;

converting the at least one voltage into at least one analog frequency;

converting the at least one analog frequency into at least one digital frequency;

determining at least one intensity profile from the at least one digital frequency; and determining at least one component of the substance in response to the determined at least one intensity profile.

EXAMPLE 13

The method of example 12, further comprising multiplexing the at least one voltage prior to converting the at least one voltage into the at least one analog frequency.

EXAMPLE 14

The method of example 12, further comprising multiplexing the at least one analog frequency prior to converting the at least one analog frequency into the at least one digital frequency.

EXAMPLE 15

The method of example 12, further comprising determining a concentration of the at least one characteristic of the substance.

EXAMPLE 16

The method of example 12, wherein determining the least one intensity profile from at least one digital frequency comprises:

determining at least one dark frequency, wherein the at least one dark frequency is determined with an electromagnetic radiation source turned off;

calculating at least one intensity gain based on the at least one dark frequency;

determining at least one digital frequency with the electromagnetic radiation source on;

determining at least one intensity profile based on the at least one digital frequency, the at least one dark frequency, and the at least one intensity gain.

EXAMPLE 17

An integrated computational element (ICE) module housed within a tool to determine at least one characteristic of a substance, the ICE module comprising:

an integrated computational element that optically processes electromagnetic radiation, wherein the electromagnetic radiation has previously interacted with the substance;

an electromagnetic radiation to voltage converter that detects the processed electromagnetic radiation using at least one channel of the electromagnetic radiation to voltage converter and further converts the detected electromagnetic radiation into at least one voltage;

a voltage to analog frequency converter operable to convert the at least one voltage into at least one analog frequency;

an analog to digital frequency converter operable to convert the at least one analog frequency into at least one digital frequency; and a processor operable to:
determine at least one intensity profile from the at least one digital frequency, and
determine at least one characteristic of the substance in response to the determined at least one intensity profile.

EXAMPLE 18

The ICE module of example 17, further comprising a multiplexer to multiplex the at least one voltage prior to converting the at least one voltage into the at least one analog frequency.

EXAMPLE 19

The ICE module of example 17, further comprising a multiplexer to multiplex the at least one analog frequency prior to converting the at least one analog frequency into the at least one digital frequency.

EXAMPLE 20

The ICE module of example 17, wherein the processor is further operable to determine a concentration of the at least one characteristic.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order or simultaneous where appropriate. Where appropriate, aspects of any of the examples described above may be combined with aspects of any of the other examples described to form further examples having comparable or different properties and addressing the same or different problems.

It will be understood that the above description of the embodiments is given by way of example only and that various modifications may be made by those skilled in the art. The above specification, examples, and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. An optical computational system to determine characteristics of a substance, the system comprising:

at least one integrated computational element (ICE) module housed within the system, at least one ICE module being placed proximate to the substance to determine at least one characteristic of the substance, at least one ICE module comprising:
an integrated computational element comprising a substrate comprising multiple stacked dielectric layers and operable to optically process electromagnetic radiation, wherein the electromagnetic radiation has previously interacted with the substance,
an electromagnetic radiation to voltage converter that detects the processed light using at least one channel of the electromagnetic radiation to voltage converter and converts the detected electromagnetic radiation into at least one voltage,
a voltage to analog frequency converter that converts the at least one voltage into at least one analog frequency,
an analog to digital frequency converter that converts the at least one analog frequency into at least one digital frequency, and
a processor operable to:
determine at least one intensity from the at least one digital frequency, and
determine at least one characteristic of the substance in response to at least one intensity profile.

2. The system of claim 1, the system further comprising a multiplexer to multiplex at least one voltage prior to converting at least one voltage into at least one analog frequency.

3. The system of claim 1, the system further comprising a multiplexer to multiplex the at least one analog frequency prior to converting at least one analog frequency into at least one digital frequency.

4. The system of claim 1, the system further comprising a multiplexer to multiplex at least one digital frequency prior to determining at least one intensity.

5. The system of claim 1, wherein the electromagnetic radiation to voltage converter is a thermopile detector array and each channel is a thermocouple.

6. The system of claim 1, wherein the electromagnetic radiation to voltage converter is a photodiode detector array and each channel is a photodiode.

7. The system of claim 1, wherein at least one voltage to analog frequency converter comprises a voltage controlled oscillator.

8. The system of claim 1, wherein to determine at least one intensity from at least one digital frequency, the processor is further operable to:
determine at least one dark frequency, wherein at least one dark frequency is determined with an electromagnetic radiation source turned off,
calculate at least one intensity gain based on at least one dark frequency,
determine at least one digital frequency with the electromagnetic radiation source on, and
determine at least one intensity based on at least one digital frequency, at least one dark frequency, and at least one intensity gain.

9. The system of claim 1, wherein at least one of the electromagnetic radiation to voltage converter, the voltage to analog frequency converter, and the analog to digital frequency converter comprises an application-specific integrated circuit.

10. The system of claim 1, wherein the processor is further operable to determine a concentration of the at least one characteristic.

11. The system of claim 1, wherein at least one of the electromagnetic radiation to voltage converter, the voltage to analog frequency converter, and the analog to digital frequency converter comprises a circuit fabricated using at least one of a silicon on sapphire process and a silicon on insulator process.

12. A method to determine at least one characteristic of a substance, the method comprising:
placing at least one integrated computational element (ICE) module proximate to the substance, wherein the at least one ICE module is housed within a tool;
processing, by an integrated computational element in the ICE module, electromagnetic radiation, wherein the electromagnetic radiation has previously interacted with the substance and comprises a substrate comprising multiple stacked dielectric layers;
detecting the processed electromagnetic radiation by at least one channel of an electromagnetic radiation to voltage converter in the ICE module;
converting the detected electromagnetic radiation into at least one voltage;
converting at least one voltage into at least one analog frequency;
converting at least one analog frequency into at least one digital frequency;
determining at least one intensity from at least one digital frequency; and
determining at least one characteristic of the substance in response to the determined at least one intensity profile.

13. The method of claim 12, further comprising multiplexing at least one voltage prior to converting at least one voltage into at least one analog frequency.

14. The method of claim 12, further comprising multiplexing at least one analog frequency prior to converting at least one analog frequency into at least one digital frequency.

15. The method of claim 12, further comprising determining a concentration of at least one characteristic.

16. The method of claim 12, wherein determining least one intensity profile from at least one digital frequency comprises:
determining at least one dark frequency, wherein at least one dark frequency is determined with an electromagnetic radiation source turned off;
calculating at least one intensity gain based on at least one dark frequency;
determining at least one digital frequency with the electromagnetic radiation source on;
determining the at least one intensity profile based on at least one digital frequency, at least one dark frequency, and at least one intensity gain.

17. An integrated computational element (ICE) module housed within a tool to determine at least one characteristic of a substance, the ICE module comprising:
an integrated computational element comprising a substrate comprising multiple stacked dielectric layers and operable to optically process electromagnetic radiation, wherein the electromagnetic radiation has previously interacted with the substance;
an electromagnetic radiation to voltage converter that detects the processed light using at least one channel of the electromagnetic radiation to voltage converter and further converts the detected electromagnetic radiation into at least one voltage;
a voltage to analog frequency converter that converts at least one voltage into at least one analog frequency;

an analog to digital frequency converter that converts at least one analog frequency into at least one digital frequency; and a processor operable to:
- determine at least one intensity profile from at least one digital frequency, and
- determine at least one component of the substance in response to the determined at least one intensity profile.

18. The ICE module of claim 17, further comprising a multiplexer to multiplex at least one voltage prior to converting at least one voltage into at least one analog frequency.

19. The ICE module of claim 17, further comprising a multiplexer to multiplex at least one analog frequency prior to converting at least one analog frequency into at least one digital frequency.

20. The ICE module of claim 17, wherein the processor is further operable to determine a concentration of at least one characteristic.

* * * * *